United States Patent
Ben Chaabane et al.

(10) Patent No.: US 11,274,122 B2
(45) Date of Patent: Mar. 15, 2022

(54) **SEPARATION OF ENZYMES FROM *TRICHODERMA REESEI* BY FILTER PRESS AND TANGENTIAL FILTRATION ON A CERAMIC MEMBRANE**

(71) Applicants: IFP Energies Nouvelles, Rueil-Malmaison (FR); Institut National De La Recherche Agronomique, Paris (FR)

(72) Inventors: Mohamed Fadhel Ben Chaabane, Paris (FR); Romain Rousset, Lyons (FR)

(73) Assignees: IFP Energies Nouvelles, Rueil-Malmaison (FR); Institut National De La Recherche Agronomique, Paris (FR)

( * ) Notice: Subject to any disclaimer, the term of this patent is extended or adjusted under 35 U.S.C. 154(b) by 0 days.

(21) Appl. No.: 16/318,446

(22) PCT Filed: Jul. 11, 2017

(86) PCT No.: PCT/EP2017/067470
§ 371 (c)(1),
(2) Date: Jan. 17, 2019

(87) PCT Pub. No.: WO2018/015228
PCT Pub. Date: Jan. 25, 2018

(65) Prior Publication Data
US 2020/0031864 A1   Jan. 30, 2020

(30) Foreign Application Priority Data
Jul. 22, 2016   (FR) ...................... 1657030

(51) Int. Cl.
| | | |
|---|---|---|
| *C07K 1/34* | (2006.01) | |
| *C12N 1/02* | (2006.01) | |
| *C12N 1/14* | (2006.01) | |
| *C12N 9/42* | (2006.01) | |
| *C12P 21/00* | (2006.01) | |

(52) U.S. Cl.
CPC .................. *C07K 1/34* (2013.01); *C12N 1/02* (2013.01); *C12N 1/14* (2013.01); *C12N 9/2437* (2013.01); *C12P 21/00* (2013.01)

(58) Field of Classification Search
CPC ... C07K 1/34; C12N 1/02; C12N 1/14; C12N 9/2437; C12P 21/00; C12P 7/06; Y02E 50/10
See application file for complete search history.

(56) References Cited

U.S. PATENT DOCUMENTS

2014/0295525 A1*  10/2014  Kurihara ............. B01D 61/145
                                                      435/209
2017/0211051 A1*   7/2017  Ben Chaabane ........ C12N 1/14

FOREIGN PATENT DOCUMENTS

WO        2016/016182 A1     2/2016

OTHER PUBLICATIONS

Boer et al. Characterization of Trichoderma reesei Cellobiohydrolase Cel7A Secreted from Pichia pastoris Using Two Different Promoters. Biotechnology and Bioengineering, vol. 69, No. 5, Sep. 5, 2000, p. 486-494.*
Zhao et al. Production of cellulase by Trichoderma reesei from pretreated straw and furfural residues. RSC Adv., 2018, 8: 36233-36238).*
International Search Report dated Sep. 25, 2017 issued in corresponding PCT/EP2017/067470 application (3 pages).
S.S. Rashid et al., "Separation of Cellulase Enzyme from Fermentation Broth of Palm Oil Mill Effluent by Ultrafiltration Process", International Journal of Chemical, Environmental & Biological Sciences, vol. 1, Issue 3 (2013) pp. 501-506.
X. Yang et al., "Purification of Cellulase Fermentation Broth Via Low Cost Ceramic Microfiltration Membranes With Nanofibers-Like Attapulgite Separation Layers", Separation and Purification Technology, vol. 175 (2017) pp. 435-442.

* cited by examiner

*Primary Examiner* — Iqbal H Chowdhury
(74) *Attorney, Agent, or Firm* — Millen, White, Zelano & Branigan, PC

(57) ABSTRACT

The invention relates to a method for separating, from a culture medium, an enzymatic cocktail and the fungus *Trichoderma Reesei*, the culture medium resulting from enzyme production by the fungus, method in which: said culture medium is subjected, in a period of no longer than 30 h from the halting of production, to a separation on a filter press lined with a fabric having a porosity of 3-20 μm, so as to obtain a filtrate having a corrected optical density OD at 600 nm of less than 2.5; and the liquid phase obtained is subjected to tangenital micro-filtration on a ceramic membrane having a cut-off limit of 0.5 to 1.4 μm, so that the corrected OD at 600 nm does not exceed 0.1.

15 Claims, 2 Drawing Sheets

SEPARATION OF ENZYMES FROM *TRICHODERMA REESEI* BY FILTER PRESS AND TANGENTIAL FILTRATION ON A CERAMIC MEMBRANE

The invention relates to a process for separating cellulolytic and hemicellulolytic enzymes contained in a culture medium comprising a *Trichoderma reesei* filamentous fungus.

The invention comes in particular within the scope of the processes for producing sugar, biofuels, or biochemical molecules from lignocellulosic biomass.

This type of process comprises a step of enzymatic hydrolysis of the biomass pretreated with an enzymatic cocktail produced for example by the filamentous fungus *Trichoderma reesei*. The present invention relates to the separation of this enzymatic cocktail and of the filamentous fungus *Trichoderma reesei*.

There are numerous separation techniques that are used alone or in series.

PRIOR ART

In the context of the separation of enzymes from fungus, present application WO-2016/16182 by the applicant recommends the following series:
- a first separation by decanting. In some cases, flocculants may be added in order to increase the efficiency of the separation,
- a second separation by centrifugation in order to reduce the pellet (also referred to as pellet content),
- a microfiltration (tangential filtration) in order to remove any trace of microorganism,
- a final step of ultrafiltration in order to concentrate the enzymes.

The decanting and the centrifugation continuously used in industrial processes are processes of solid/liquid separation as a function of their difference in density and by subjecting the medium to a centrifugal force.

The decanters are centrifugal machines equipped with a screw, the bowl of which rotates about a horizontal axis. They are mainly used to clarify (two-phase decanter) mixtures with large pellets or with a high suspended matter content (greater than 15% and often about 30%, and even up to 60%). Decanting makes it possible to reduce this content to approximately 5%. The pellet is measured by centrifuging a sample at 4000 G for 5 minutes. It corresponds to the percentage of the volume occupied by the solid relative to the total volume of the sample.

Certification is used with solutions which have a pellet of less than 15% and makes it possible to reduce this pellet to values of less than 2%, or even than 1%. Centrifugation makes it possible to clarify the cloudy liquid resulting from the decanting.

It is used in many fields: water treatment, food-processing, biotechnology, pharmaceutical industry, etc.

The separation processes by tangential filtration or ultrafiltration are implemented according to the size of the elements to be separated. They use membranes.

Thus, in the case of microfiltration, the particles have a size ranging from 0.1 µm to 10 µm. This process is used to separate, for example, microorganisms such as filamentous fungi. For economical reasons, it is usually organic membranes that are used.

Ultrafiltration is used to separate objects which have diameters of between 1 and 100 nm. Such membranes allow small molecules (water, salts) to pass through and stop high-molecular-weight molecules (polymers, proteins, etc.). They will be used to concentrate, for example, proteins or enzymes.

The factors which can have an impact on the separation performance levels are essentially the size of the molecules, the shape of the molecules, their charge, the nature of the membrane and the operating conditions.

The membranes are characterized by their physicochemical nature. In general, three main classes of membranes are distinguished:
- organic (natural or synthetic) membranes,
- mineral (inorganic or ceramic) membranes,
- composite membranes.

Organic membranes are made from cellulose polymer (for example cellulose acetate). They have low production costs, but cannot be used to separate cellulases that may hydrolyze them.

Organic membranes based on synthetic polymers, such as nylon and polysulfone, have many advantages compared with the preceding ones and are the most widely used for separating enzymes (proteins).

Mineral membranes have very good chemical resistance, mechanical strength and heat resistance, but are more expensive than organic membranes (approximately 10 times more expensive). They are used in biotechnologies in various processes, such as clarification of fruit juices, elimination of bacteria in milk or clarification of alcoholic beverages (wine, beer, cider). They also have applications in water treatment.

Finally, composite membranes are composed of a polymer portion deposited on another portion, which is microporous. The latter membranes have been developed essentially for reverse osmosis.

There is an abundance of information in the prior art in this field.

U.S. Pat. No. 3,398,055 teaches the separation and purification of cellulases produced by *Trichoderma reesei*. The fungus is separated with a rotary filter under vacuum. The enzymes are separated using cotton and are eluted with a basic solution.

Patent application US-2014/0295525 proposes a 2-step separation of the enzymes of the fungus *Trichoderma*. The process describes the concentration of the enzymes in two ultrafiltration steps, the enzymes having previously undergone a solid/liquid separation step. In a first separation step by ultrafiltration, the membrane has an MWCO of from 100 000 (Da) to 200 000 (Da), i.e. approximately 0.01 µm to 0.02 µm cutoff threshold. The retentate passes into a second ultrafiltration step on a membrane having an MWCO of from 5000 to 50 000, and the 2 liquids containing the enzymes are mixed.

The patent indicates that this method makes it possible to solve the problems of fouling of the membrane and of aggregation of the cellulases during a single ultrafiltration step, even when it is preceded by a separation of solid particles in a ceramic filter or a nonwoven material.

In the patent, retention of the enzymes in the retentate is noted, although the size of said enzymes is between 10 kDa and 100 Da. This patent thus essentially describes an optimization of the enzyme concentration step.

In the context of the concentration of the enzymatic cocktail from the fungus *Trichoderma reesei*, it has been possible to note, surprisingly, the existence of this enzyme retention phenomenon with organic membranes which have a size of 0.8 µm, and therefore have pores that are 40 to 80 times larger than those described by patent application US-2014/0295525. This greatly penalized the enzyme separation yield.

The invention proposes a separation process comprising
a step of separation of the fungus *Trichoderma reesei* on
a filter press which must advantageously be carried out
in the 30 or 24 hours that follow the production,
then a step of microfiltration on a mineral membrane,
optionally followed by a step of concentration on a
mineral or organic membrane.

It has been noted that the series of a separation on a filter press followed by a microfiltration on a mineral membrane, and optionally by an ultrafiltration on a mineral membrane, makes it possible to obtain results that are particularly good in terms of yield and efficiency.

SUMMARY OF THE INVENTION

Figure 1:
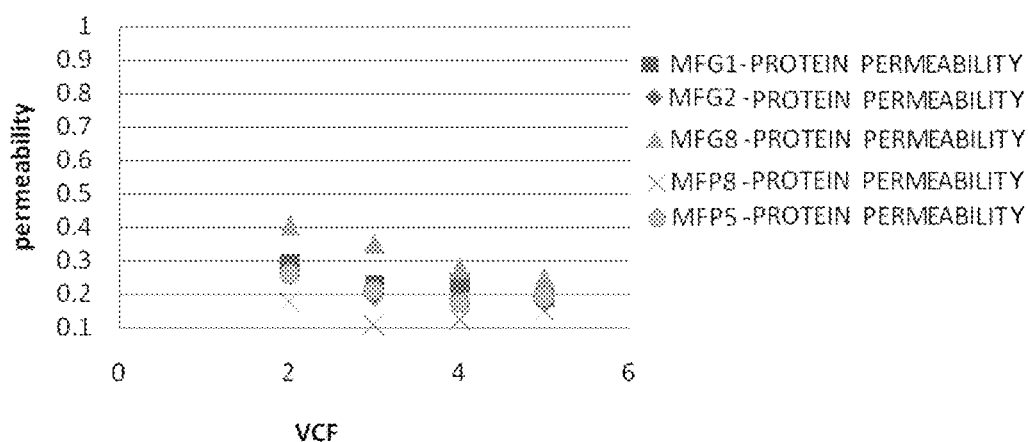
FIGS. 1 and 2 present the results of the laboratory tests carried out with organic membranes having porosities.

More specifically, the invention proposes a process for separating, from a culture medium, an enzymatic cocktail and the fungus *Trichoderma reesei*, the culture medium resulting from a production of enzymes by the fungus, in which process
said culture medium is subjected, within a period of less than or equal to 30 h, preferably less than or equal to 24 h, from halting the production, to a separation on a filter press lined with a fabric having a porosity of 3-20 μm, so as to obtain a filtrate having a corrected optical density OD at 600 nm of less than 2.5; and
the liquid phase obtained is subjected to tangential microfiltration on a ceramic membrane having a cutoff threshold of between 0.5 and 1.4 μm, so that the corrected OD 600 nm does not exceed 0.1.

Advantageously, said culture medium is subjected to the separation on a filter press without prior cooling. Preferably, the culture medium is not subjected to decanting and/or centrifugation before being separated on a filter press.

The separation on a filter press and the microfiltration are carried out at 20-30° C., preferably 22-27° C.

Advantageously, the filtrate is recycled to the culture medium feeding the filter press in a proportion of at most 10% by weight.

At the end of the separation on a filter press (i.e. after compacting), 5-10% by weight of cake (the solids content of the cake is at least 20% by weight, generally between 20% and 65% or 20-45%, often about 25-35%) and 90-95% by weight of filtrate are generally obtained. The pellet (percentage of the volume occupied by the solid relative to the total volume of the sample, measured by centrifuging a sample at 4000 G for 5 minutes) of the filtrate resulting from the filter press is less than 1.5%.

Advantageously, the microfiltration of the filtrate obtained at the end of the filter press is carried out within a period of at most 30 h, and preferably at most 24 h.

Preferably, said filtrate resulting from the filter press is subjected to the microfiltration without prior cooling.

Preferably, the tangential microfiltration is carried out on a ceramic membrane having a cutoff threshold of between 0.8 and 1.4 μm.

Preferably, the liquid phase obtained after microfiltration is subjected to ultrafiltration, preferably on a ceramic membrane, and even more preferably on a ceramic membrane having a cutoff threshold of between 5 and 15 kDa.

Preferably, the liquid phase obtained after microfiltration is subjected to ultrafiltration within a period of at most 48 h, preferably at most 24 h.

In one preferred embodiment, the separated enzymatic cocktail is brought into contact with a lignocellulosic biomass that has been pretreated, preferably by steam explosion, in order to carry out an enzymatic hydrolysis and to obtain sugary juices, said sugary juices undergo ethanolic fermentation, the enzymatic hydrolysis and the fermentation being carried out separately or simultaneously, and the ethanol produced is separated by distillation.

DETAILED DESCRIPTION OF THE INVENTION

Production Step

The enzymatic cocktail is produced by *Trichoderma reesei* in a conventional production line by aerated fermentation.

The process for producing the enzymatic cocktail begins with a propagation phase, generally carried out in small reactors of increasing size, for the purpose of multiplying the filamentous fungus and of limiting the duration of the lag phase and the contamination risks.

When this production is judged to be sufficient (fungus concentration greater than 10 g/l, preferably greater than 15 g/l), the culture medium is transferred into the final reactor of large volume.

The enzyme production process comprises two phases:
a phase a) of growth of said microorganism in the presence of at least one carbon-based growth substrate in an aerated closed reactor, said growth phase being carried out with a carbon-based growth substrate concentration of between 10 and 90 g/l;
a phase b) of production of the enzymatic cocktail, in which at least one carbon-based inducer substrate is introduced, said carbon-based inducer substrate being chosen from the group formed by lactose, cellobiose, sophorose, the residues obtained after ethanolic fermentation of the monomeric sugars of the cellulose-based biomass enzymatic hydrolysates, and/or a crude extract of water-soluble pentoses originating from the pretreatment of a cellulose-based biomass, said production phase being carried out with a carbon-based production substrate concentration of between 150 and 400 g/l.

The microorganisms used in the process for producing an enzymatic cocktail according to the invention are fungal strains belonging to the species *Trichoderma reesei*.

The most effective industrial strains are the strains belonging to the species *Trichoderma reesei*, which are modified to improve the enzymatic cocktail by means of mutation-selection processes, for instance the strain IFP CL847 (French patent FR-B-2 555 803). The strains improved by genetic recombination techniques may also be used. These strains are cultured in stirred and aerated reactors under conditions compatible with their growth and the production of the enzymes.

Said carbon-based growth substrate for said microorganism that is used in said growth phase a) of the process according to the invention is advantageously chosen from industrial soluble sugars, and preferably from glucose, lactose, xylose, liquid residues obtained after ethanolic fermentation of the monomeric sugars of the enzymatic hydrolysates of lignocellulosic materials, and extracts of the hemicellulose-based fraction in the form of monomers originating from pretreated lignocellulosic substrate, used alone as a mixture.

Depending on its nature, said carbon-based growth substrate is introduced into the closed reactor before sterilization or is sterilized separately and introduced into the closed reactor after sterilization of the latter.

Said carbon-based growth substrate is used in said growth phase a) at an initial concentration usually between 20 and 90 g of carbon-based substrate per liter of reaction volume.

Preferably, said growth phase a) is carried out over a period of between 30 and 70 h, preferably between 30 and 40 h.

Preferably, said growth phase a) is carried out at a pH of 4.8 and at a temperature of 20-30° C., generally 22-27° C., preferably about 27° C.

Said carbon-based inducer substrate used in said production phase b) is advantageously fed in fed-batch phase mode with a limiting flow of between 30 and 80 mg per gram of cells and per hour. The temperature is generally the same as in step a).

At the end of the enzyme production step, a medium containing a solids concentration of between 10 and 45 g/l (corresponding to the dry fungus) is generally obtained. The pellet measured after centrifugation (4000 G, 5 minutes) is greater than 15% and often about 30%, and even up to 60%. It corresponds to the percentage of the volume occupied by the solid relative to the total volume of the sample.

It is observed that the fungus retains a considerable portion of liquid.

The aim of the invention is to separate the enzymes from the fungus and then optionally to concentrate them.

Solid/liquid separation steps in which the fungus is separated from the liquid

The liquid contains the enzymes and the residual salts.

The test carried out by the applicant have shown that a separation on a filter press followed by a microfiltration (MF) on a ceramic membrane gives better results than the prior art solutions, whether in terms of yield or in terms of efficiency.

Moreover, the tests have generally shown that, for concentrating the enzymes, an ultrafiltration (UF) on a ceramic membrane is substantially more efficient than on an organic membrane.

According to the invention, the culture medium is subjected to a separation on a filter press which makes it possible to maximize the enzyme recovery.

It is very advantageously carried out before autolysis of the fungus develops. This is because this autolysis can greatly penalize the efficiency of the separation by filter press. In the case of *Trichoderma reesei*, this period of time is less than or equal to 30 h, and preferably less than or equal to 28 h, and even more preferably less than or equal to 24 h.

At the end of this separation on a filter press, a cake containing the fungus and a liquid containing the enzymes are obtained.

The liquid obtained is subjected to a tangential microfiltration on a ceramic membrane and then optionally to an ultrafiltration, preferably by tangential filtration.

This is because it has been possible to note that a microfiltration on organic membranes results in a significant retention of enzymes, which is detrimental to the separation yield. This phenomenon is surprising since the pores are up to 100 times larger than the size of the largest enzymes produced. It has not been possible to provide an explanation for this phenomenon. On the other hand, it has also been noted that this phenomenon is limited when mineral membranes are used. Thus, the enzyme recovery yield is at a high level.

The separation by filter press, the microfiltration and the ultrafiltration are explained in detail below.

Separation on a Filter Press:

As soon as the production is ended, the aeration and the pH regulation are stopped. A preservative is advantageously added, for example sodium benzoate.

The production is stopped when all of the sugar of the fed-batch phase is consumed or when the basic speed of consumption (which is proportional to the speed of protein production) has slowed down (speed less than 30% or more).

The separation on the filter press is carried out within the period before autolysis.

It has been noted that it is important to maintain the temperature below 40° C. and preferably below 30° C. Above this, the separation is much less efficient.

There is no cooling step before the separation on a filter press. This means that cooling is not sought; it may be that there is a slight drop in temperature during the transfer between the unit in which the production step takes place and the filter-press unit; this drop may be 3° C. or less. Thus, the separation is often carried out at substantially the same temperature as that of the reduction phase of step a), i.e. a temperature of 17 to 30° C. or else 20-30° C., generally 22-27° C., and usually about 25° C. This is generally ambient temperature.

The filter press is lined with a fabric, and generally has no membrane plate. The porosity of the fabrics is between 3 and 20 μm, preferably between 3 and 7 μm and preferably 5 μm. From 5% to 10% by weight of cake and 90% to 95% by weight of filtrate are generally obtained.

The separation on a filter press can be carried out in one or 2 steps.

The separation on a filter press is generally carried out in 2 steps: a first step of filtration at a pressure P1 and a second step of compacting at a pressure P2 higher than P1. Generally, the pressure P1 is between 1.2 and 6 bar and P2 is between 5 and 10 bar.

When the separation is carried out in a single step, there is no compacting, but only a step carried out at P1.

The dryness of the cakes depends on the pressure that is applied.

The objective is to recover a maximum amount of filtrate that is as clear as possible.

To do this, it is recommended to recycle the first filtrate fractions (generally the most cloudy) into the feed tank. This recycling must not exceed 10% of the filtrate volume. In the case of good separation and of a permeable cake, it is recommended to add water to the cake in order to wash it and to recover a maximum amount of proteins.

Another way, which can be used alone or consecutively to employ the recycling described above, is to allow the fungus which is in the cake to lyse, this being after a cooling step. The fungus then releases enzymes which are then recovered. This process is described in application WO-2016/016182.

The separation is carried out so as to obtain a liquid (or suspension) having a corrected OD (optical density) 600 nm of less than 2.5 (corrected means minus the absorbance of an equivalent 0.22 μm filtrate). The measurement is carried out on a sample with conventional laboratory spectrometry.

The pellet (4000 g/5 min) is generally less than 1.5%.

Microfiltration with Mineral Membranes

This step must make it possible to remove all of the fungi from the filtrate. It is carried out in such a way that the corrected OD 600 nm does not exceed 0.1 (minus the absorbance of an equivalent 0.22 µm filtrate).

Preferably, and in the same way as for the separation by filter press, the filtrate is subjected to the microfiltration within a period of at most 30 h or at most 28 h or preferably of at most 24 h. Usually, the microfiltration can be carried out on-line with the filter press.

With regard to the temperature, it is preferably not decreased (no cooling sought). This makes it possible to preserve a satisfactory product flow rate. The temperature is thus generally between 17 and 30° C. or else 20 and 30° C. and generally 22-27° C., and usually about 25° C. This is generally ambient temperature.

The membranes to be used have a cutoff threshold of between 0.5 and 1.4 µm, preferably of between 0.6 and 1.4 µm and preferably between 0.8 and 1.4 µm.

The enzyme yield can be maximized by diafiltration (addition of water to the retentive then passage through microfiltration).

Ultrafiltration with Mineral or Organic Membranes

This step makes it possible to concentrate the enzymes produced by the fungus, in particular by *Trichoderma reesei*. The enzymatic cocktail is a complex mixture of several enzymes, the size of which ranges between $1 \times 10^4$ g/mol (10 kDa) and $10 \times 10^4$ g/mol (100 kDa).

This ultrafiltration step is carried out at a temperature generally of between 20-30° C., and generally of 22-27° C., and usually of about 25° C. It is always advantageous to carry it out as closely as possible (in time) to the microfiltration. A maximum period of 48 h is recommended, and this period is preferably less than or equal to 24 h.

This step makes it possible to concentrate the proteins of interest to 150 g/l+/−10 g/l. The value of the volumetric concentration factor VCF to be achieved depends on the initial protein concentration.

An additional dose of preservative can be added to the retentate at the end of this step. The addition of sodium benzoate between 0.1% and 0.35% will for example be recommended.

It is preferable to use mineral membranes for the ultrafiltration. Tubular ceramic membranes with cutoff thresholds of between 5 and 15 kDa and preferably 8-12, usually about 10 kDa, will for example be used.

In some cases, organic membranes may be used, but with care and only under the conditions recommended by the suppliers.

Particularly advantageously, the process according to the invention is used to separate the enzymes in a process for producing, from lignocellulosic biomass, sugary juices, biofuels (such as ethanol) or biochemical molecules.

These processes comprise the steps of pretreatment of the lignocellulosic biomass (for example steam explosion); the pretreated biomass is subjected to enzymatic hydrolysis in the presence of enzymes (secreted by *Trichoderma reesei*), the hydrolysate loaded with sugary juices is subjected to fermentation (for example alcoholic fermentation) and the desired products (for example the alcohol) are separated (for example by distillation).

A process in which the invention applies particularly well comprises pre-treatment of the lignocellulosic biomass by steam explosion; the pretreated biomass is subjected to enzymatic hydrolysis in the presence of enzymes secreted for example by *Trichoderma reesei* from which they were separated according to the process of the invention, the hydrolysate loaded with sugary juices is subjected to alcoholic fermentation and the ethanol is separated by distillation.

The enzymatic hydrolysis and the fermentation may be carried out separately or simultaneously.

It should be noted that the ultrafiltration step proved to be needless most of the time in the case of a plant which produces ethanol with in-situ production of enzymes.

EXAMPLES

Example 1 demonstrates the poor enzyme permeability obtained with microfiltration with organic membranes. This problem is solved in example 2 with the use of mineral membranes. Example 3 compares two series carried out either with a conventional separation process or with the process described in the patent. Example 4 presents the complete balance of a separation on a large volume.

Example No. 1: Tests of Microfiltration on an Organic Membrane (Comparative)

The culture medium to be treated resulting from the production phase has the following composition:
40 g/l of proteins
20 g/l of biomass (fungus *T. reesei*).

After having undergone separation via a filter press, the filtrate is tested on various microfiltration membranes.

Figure 2:
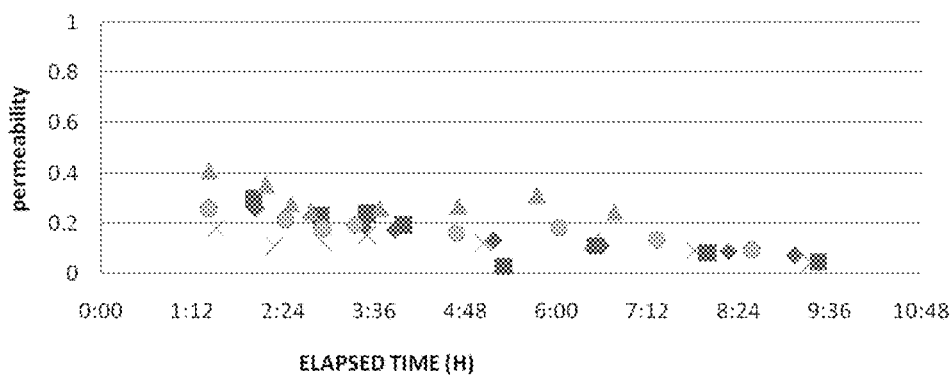

FIGS. 1 and 2 present the results of the laboratory tests carried out with organic membranes having porosities ranging from 0.1 to 0.8 µm: membranes MFG1: cutoff threshold of 0.1 µm (polysulfone), MFG2: 0.2 µm (polysulfone), MFG8: 0.8 µm (polysulfone), MFP5: 0.5 µm (fluoro).

VCF represents the volumetric concentration factor.

The low permeability of these membranes to enzymes is noted.

The permeability is defined as being the ratio between the concentration of the enzymes in the permeate (which passes through the membrane) and the concentration in the retentate (which remains).

Example 2: Tests of Microfiltration on a Ceramic Membrane

The same filtrate is used with 4 membranes with the cutoff thresholds of 0.14, 0.45, 0.8 and 1.4 µm.

The method used was to test 4 cutoff thresholds in parallel for each filtration. The tool used is a pilot filtration unit which makes it possible to receive 4 different membranes in one and the same casing. It has one permeate outlet per membrane and a single retentate loop. It thus makes it possible to study, in parallel, the variations in permeate flow rates for 4 membranes and to produce samples.

The measurements of the enzyme concentrations reveal disparities.

The filtrate resulting from the filter press has an enzyme concentration of 38.2 g/l. The final retentate was quantitatively determined at 44.3 g/l.

There was thus a slight concentration of the retentate, which suggests a retention by one or more membranes. The enzyme concentrations of the 4 permeates are the following:

| Cutoff threshold (µm) | 0.14 | 0.45 | 0.8 | 1.4 |
|---|---|---|---|---|
| Enzyme concentration in the permeate (g/l) | 17.1 | 17.0 | 33.9 | 38.1 |

Compared with the initial retentate, it is seen that the concentrations obtained by filtration at 0.8 and 1.4 µm are close to the concentrations of the initial solution. On the other hand, there is clearly enzyme retention for the cartridges at 0.14 and 0.45 µm. The protein concentration obtained with the mineral membrane having a cutoff threshold of 0.8 µm is approximately 4.3 times higher than the protein concentration obtained with the organic membrane having the same cutoff threshold (example 2).

Example 3

Example 3 makes it possible to compare two series carried out either with a conventional process or with the process of the patent.

The culture medium to be treated resulting from the production phase has the following composition:
39 g/l of proteins
16.5 g/l of biomass (fungus T. reesei).

Example 3 a: conventional series of a decanter, of a centrifuge and of MF (microfiltration) on an organic membrane and UF (ultrafiltration) on an organic membrane.

The following performance levels are obtained:
decanting: reduction of the pellet from 30% to 5%, but significant loss of proteins. Yield 70%.
Centrifugation: reduction of the pellet from 5% to 1.5% without significant loss. Yield 95%.
Organic MF at 0.8 µm: reduction of the pellet from 1.5% to ~0%. Low permeability of 0.3. Yield 50%.
Organic UF 10 kDa: enzyme concentration at 200 g/l. Yield 80%.

The overall yield of this series is 27%. It is possible to get close to a 50% yield by recycling the pellets from the decanting and centrifugation steps and the retentate from the MF step and subjecting them to a further separation cycle (centrifugation, MF, UF).

Example 3b According to the Invention

Series of a separation on a filter press then on MF on a ceramic membrane and UF on a ceramic membrane.
The following performance levels are obtained:
Separation on a filter press: reduction of the pellet from 30% to 1.5% without significant loss. Yield 95%
Ceramic MF (1.4 µm): reduction of the pellet from 1.5% to ~0%. High permeability of 0.9. Yield 90%.
Ceramic UF 10 kDa: enzyme concentration at 200 g/l. Yield 90%.

The overall yield without carrying out any recycling of this series is 77%.

In the light of these results, it is noted that the UF step is needless in the case of a plant which produces ethanol with an in-situ production of enzymes. Consequently, the yield is 86%.

Moreover, the MF filtration is much more efficient on a ceramic membrane then on an organic membrane. Furthermore, the yield on a ceramic membrane, whether it is by MF or UF, is much higher than the yield with organic membranes.

Example No. 4: Pilot Test with the Series According to the Invention

This test uses a culture medium produced in a 6 m$^3$ reactor. Its characteristics are the following:
Mass of the culture medium: 4260 kg
Protein concentration: 38 g/l
Biomass concentration: 15 g/l Separation on a Filter Press:

The separation was carried out immediately after the production step, and without cooling the product. The temperature is 27° C.

In this step, it is sought to eliminate the majority of the fungus by separation on a filter press.

The tool used comprises 10 plates with an overall filtration surface area of 3 m$^2$. This makes it possible to form, per batch, 10 fungal cakes 30 mm thick and having a total volume before compacting of 30 liters. The fabric used is a multifilament fabric having a porosity of 5 µm. The separation is carried out in three steps:

The first step consists of a filtration with an upstream pressure of 5 bar with monitoring of the filtration flow rate over time.

During the second step, the feeding of the filter press is stopped, and the fungal cakes are compacted by applying a higher pressure (9 bar). This second step presses the fungus and maximizes the enzyme recovery.

the third step consists of dismantling (recovery) of the cakes which are weighed.

It should be noted that it would have been possible to perform washing of the cake in order to minimize the losses, or to leave the fungus to lyse, but this was not done in the case of this example.

A total of 14 filtrations/compactings were necessary in order to treat all of the culture medium (4260 kg).

The following table presents the mass balance separation.

| Variable | Value | Unit |
| --- | --- | --- |
| Total feed amount | 4260 | kg |
| Amount of filtrate recovered without compacting | 3681.5 | kg |
| Amount of filtrate recovered by compacting | 210 | kg |
| Total amount of cakes | 211.76 | kg |
| Quantified losses | 30 | kg |
| Mass balance | 97 | % |

Figure 3:
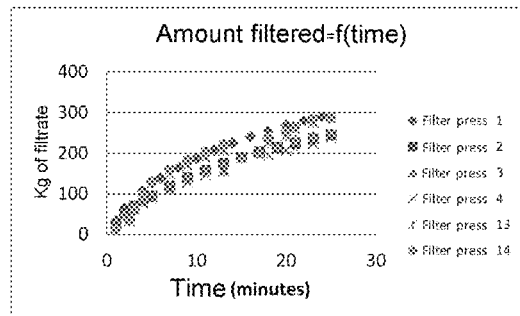
FIG. 3 presents the change in the amount filtered as a function of time.
Figure 4:
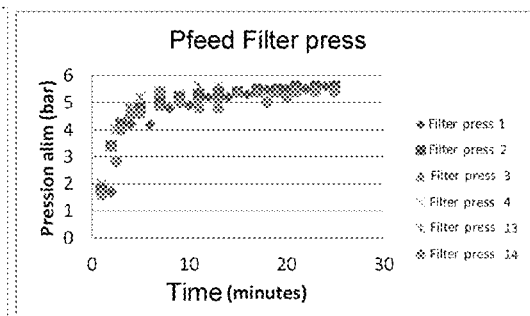
FIG. 4 the change in the amount filtered as a function of the feed pressure.

FIG. 3 presents the change in the amount filtered as a function of time and figure for the change in the amount filtered as a function of the feed pressure.

In the first step (filtration at 5 bar), the batch time is 25 minutes.

During the first minutes, the filtration flow rate is high (between 500 and 700 l/m$^2$/h). The fungus "sticks" to the fabric and will serve as filtering media. The pressure increases and the filtration flow rate decreases. It is in general decided to stop the filtration when the flow rate appears to be too low compared with the initial flow (for example, less than 10% or 20%) and as a function of the initial objective of the filtration time.

It is noted that there is no significant difference between the various batches produced. This shows that the ability of the product to be filtered did not change during the operation (which lasted less then 12 hours in total).

The average mass per batch before compacting is 263±30 kg. The average filtration flow rate is 210 kg/m$^2$/h.

The compacting is then carried out (9 bar), which compacting lasted on average 10 minutes and made it possible to recover on average 15 kg of liquid per batch with an average flow rate of 30 kg/m$^2$/h. The average mass of cake obtained per batch is 15±1.5 kg.

The weight percentage of cake relative to the filtrate is on average 5.4% and the average SC (solids content) thereof is 25% by weight, that is to say a protein loss in this step of 4.05% by weight if the cake is not washed.

The protein recovery yield after the filter press step is 95.4%.

Separation by Microfiltration on a Mineral Ceramic:

The filtrate resulting from the filter press was then divided up into several samples which are treated by microfiltration on mineral membranes having porosities of 0.8 and 1.4 µm. The objective of the test is to compare their performance levels on the filter-press filtrate containing enzymes and fungi with a targeted volumetric concentration factor of 10. The microfiltration is followed by a diafiltration which makes it possible to minimize the protein losses (addition of water corresponding to 5 volumes of retentate).

The microfiltration tool comprises 3 membranes having a filtration surface area of 0.33 m² on each casing.

The first test made it possible to select the 1.4 µm membrane which has a better filtration performance level than the 0.8 µm membrane at the same transmembrane pressure. Indeed, the flow of permeate stabilizes at 100 l/m₂/h for the first and at 60 l/m₂/h for the second up to a volumetric concentration factor (VCF) of 7.5. The two membranes made it possible to clarify the product (no fungal growth on the permeate plated out on PDA medium).

Figure 5:
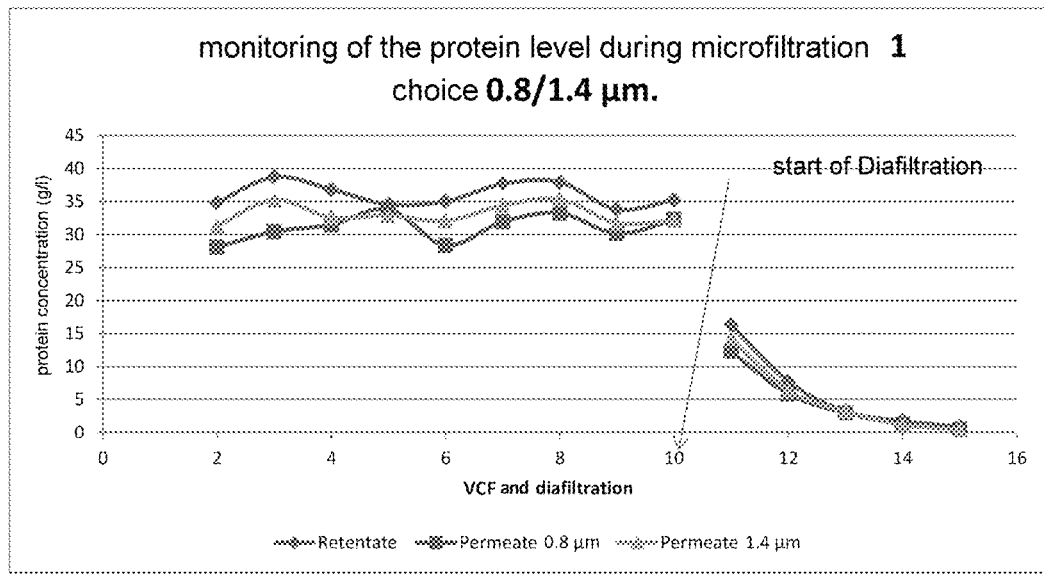
FIG. 5 represents the change in protein concentrations in the retentate and the permeates.

FIG. 5 represents the change in protein concentrations in the retentate and the permeates. It shows that the permeability of the two membranes with respect to proteins is very good. The permeability of the membranes at 1.4 µm is better and is greater than 0.9. It is recalled that it was 0.2-0.4 with the organic membranes even with porosities of 0.8 µm.

The protein recovery yield after MF on a mineral membrane is 93.3% relative to the initial step.

The enzymes were then concentrated by UF on a mineral membrane with a recovery yield of 92%, i.e. an overall yield of 86%.

The invention claimed is:

1. A process for separating, from a culture medium, *Trichoderma reesei* fungus from enzymes produced in the culture medium by the fungus during a production step, comprising
   a) subjecting said culture medium, within a period of 0-30 h, inclusive, from halting the production step, and at ambient temperature without prior cooling, to separation of solid and liquid phases on a filter press lined with a fabric having a porosity of 3-20 µm, whereby a liquid phase filtrate containing the enzymes having a corrected optical density (OD) at 600 nm of less than 2.5 is produced; and
   b) subjecting the liquid phase filtrate to tangential microfiltration separation of solid and liquid phases on a ceramic membrane having a cutoff threshold of between 0.8 and 1.4 µm, whereby the corrected OD at 600 nm of the liquid phase of the microfiltration product containing the enzymes does not exceed 0.1,
wherein
   the filtrate is recycled into the culture medium feeding the filter press in a proportion of at most 10% by weight,
   both the separation on the filter press (step a)) and the microfiltration of the filtrate obtained at the end of the filter press (step b)) are carried out sequentially within a period of 0-30 h, inclusive, from halting the production step, and
   the culture medium is not subjected to decanting and/or centrifugation before being separated on the filter press, and
wherein the overall yield of enzymes is at least 86%.

2. The process of claim 1, wherein said period from halting the production step is less than or equal to 24 h.

3. The process of claim 1, wherein, at the end of the separation on the filter press, 5-10% by weight of solid and 90-95% by weight of filtrate are obtained.

4. The process of claim 1, wherein a sample of the liquid phase filtrate resulting from the filter press is centrifuged at 4000 G for 5 minutes to produce a solid pellet and liquid, and wherein the pellet is less than 1.5% (percentage of the volume occupied by the solid relative to the total volume of the sample).

5. The process of claim 1, wherein said filtrate resulting from the filter press is subjected to the microfiltration without prior cooling.

6. The process of claim 1, wherein the separation on the filter press and the microfiltration are carried out at 20-30° C.

7. The process of claim 1, wherein the liquid phase obtained after microfiltration is further subjected to ultrafiltration on a second ceramic membrane having a cutoff threshold of between 5 and 15 kDa.

8. The process of claim 1, wherein the liquid phase obtained after microfiltration is further subjected to ultrafiltration, and wherein all three steps of separation on the filter press (step a)), microfiltration of the filtrate obtained at the end of the filter press (step b)), and ultrafiltration, are carried out sequentially within a period of 0-48 h, inclusive, from halting the production step.

9. The process of claim 1, further comprising
   contacting a lignocellulosic biomass that has been pretreated by steam explosion with the liquid phase of the microfiltration product containing the enzymes, whereby an enzymatic hydrolysis of the biomass produces soluble sugars, and
   ethanolic fermentation of the soluble sugars,
   wherein the enzymatic hydrolysis and the fermentation are carried out separately or simultaneously, and the ethanol produced is separated by distillation.

10. The process of claim 1, wherein the enzymes comprise cellulolytic and hemicellulolytic enzymes.

11. The process of claim 1, wherein the microfiltration of the filtrate obtained at the end of the filter press is carried out within a period of at most 24 h from halting the production step.

12. The process of claim 1, wherein the separation on the filter press and the microfiltration are carried out at 22-27° C.

13. The process of claim 1, wherein the liquid phase obtained after microfiltration is subjected to ultrafiltration within a period of at most 24 h from halting the production step.

14. A process for separating, from a culture medium, *Trichoderma reesei* fungus from enzymes produced in the culture medium by the fungus during a production step, comprising
   a) subjecting said culture medium, within a period of 0-30 h, inclusive, from halting the production step, to a separation on a filter press lined with a fabric having a porosity of 3-20 µm, whereby a liquid phase filtrate containing the enzymes having a corrected optical density (OD) at 600 nm of less than 2.5 is produced; and
   b) subjecting the liquid phase filtrate to tangential microfiltration on a ceramic membrane having a cutoff threshold of between 0.5 and 1.4 µm, whereby the corrected OD at 600 nm of the liquid phase of the microfiltration product containing the enzymes does not exceed 0.1, and has at least a 4.3 times higher protein concentration than the liquid phase of a microfiltration product obtained with an organic membrane having the same cutoff threshold, and wherein the overall yield of enzymes is at least 86%.

15. The process of claim 7, further comprising contacting a lignocellulosic biomass that has been pretreated by steam explosion with the liquid phase of the ultrafiltration product containing the enzymes, whereby an enzymatic hydrolysis of the biomass produces soluble sugars, and ethanolic fermentation of the soluble sugars, wherein the enzymatic hydrolysis and the fermentation are carried out separately or simultaneously, and the ethanol produced is separated by distillation.

* * * * *